US005591820A

United States Patent [19]

Kydonieus et al.

[11] Patent Number: 5,591,820
[45] Date of Patent: Jan. 7, 1997

[54] POLYURETHANE PRESSURE-SENSITIVE ADHESIVES

[75] Inventors: Agis Kydonieus, Kendall Park; Ladislav Bastar, North Brunswick; Kishore Shah, Bridgewater; Khosrow Jamshidi, Princeton; Tak-lung Chang, Skillman; Sheng-hung Kuo, Princeton, all of N.J.

[73] Assignee: E. R. Squibb & Sons, Inc., Princeton, N.J.

[21] Appl. No.: 437,069

[22] Filed: May 9, 1995

Related U.S. Application Data

[63] Continuation of Ser. No. 973,448, Nov. 9, 1992, abandoned.
[51] Int. Cl.⁶ .................................................. C08G 18/30
[52] U.S. Cl. .......................... 528/76; 528/77; 528/85; 528/905; 428/423.1
[58] Field of Search ........................ 528/76, 77, 85, 528/905; 428/423.1

[56] References Cited

U.S. PATENT DOCUMENTS

| | | | |
|---|---|---|---|
| Re. 31,887 | 5/1985 | Hodgson | 428/355 |
| 3,197,330 | 7/1965 | Bartell . | |
| 3,226,354 | 12/1965 | Heiss . | |
| 3,246,049 | 4/1966 | Webber . | |
| 3,437,622 | 4/1969 | Dahl | 528/77 |
| 3,515,773 | 6/1970 | Dahl . | |
| 3,532,652 | 10/1970 | Zang et al. . | |
| 3,645,835 | 2/1972 | Hodgson . | |
| 3,671,301 | 6/1972 | Dahl . | |
| 3,681,277 | 8/1972 | Scholz et al. . | |
| 3,718,622 | 2/1973 | Camilleri et al. . | |
| 3,740,366 | 6/1973 | Sanderson et al. . | |
| 3,743,617 | 7/1973 | Kest . | |
| 3,761,307 | 9/1973 | Dahl . | |
| 3,767,040 | 10/1973 | Tushaus . | |
| 3,802,988 | 4/1974 | Dahl | 156/331 |
| 3,822,238 | 7/1974 | Blair et al. . | |
| 3,846,163 | 11/1974 | Kest . | |
| 3,879,248 | 4/1975 | Kest | 156/289 |
| 3,925,283 | 12/1975 | Dahl . | |
| 3,930,102 | 12/1975 | Müller | 428/354 |
| 3,940,513 | 2/1976 | Anderson | 427/207 |
| 3,975,570 | 8/1976 | Ono et al. | 428/355 |
| 4,032,686 | 6/1977 | Emmons | 428/425 |
| 4,060,664 | 11/1977 | McGuire et al. | 428/336 |
| 4,079,028 | 3/1978 | Emmons et al. . | |
| 4,094,842 | 6/1978 | Wenzel et al. . | |
| 4,099,943 | 7/1978 | Fischmann et al. . | |
| 4,111,913 | 9/1978 | Schuhmacher et al. | 528/273 |
| 4,138,527 | 2/1979 | Malek | 428/425 |
| 4,145,511 | 3/1979 | Gilles | 528/73 |
| 4,152,309 | 5/1979 | Ijichi et al. . | |
| 4,156,066 | 5/1979 | Gould | 528/73 |
| 4,156,067 | 5/1979 | Gould | 528/73 |
| 4,181,637 | 1/1980 | Busch et al. . | |
| 4,182,827 | 1/1980 | Jones et al. | 528/60 |
| 4,194,618 | 3/1980 | Malloy . | |
| 4,207,374 | 6/1980 | Groff | 428/261 |
| 4,255,550 | 3/1981 | Gould | 528/44 |
| 4,310,509 | 1/1982 | Berglund et al. | 424/28 |
| 4,323,557 | 4/1982 | Rosso et al. | 424/28 |
| 4,353,759 | 10/1982 | Stallings | 156/64 |

(List continued on next page.)

FOREIGN PATENT DOCUMENTS

| | | |
|---|---|---|
| 80668 | 6/1983 | European Pat. Off. . |
| 81103 | 6/1983 | European Pat. Off. . |
| 103453 | 3/1984 | European Pat. Off. . |
| 122344 | 10/1984 | European Pat. Off. . |
| 196749 | 10/1986 | European Pat. Off. . |
| 208856 | 1/1987 | European Pat. Off. . |
| 250248 | 12/1987 | European Pat. Off. . |
| 271292 | 8/1988 | European Pat. Off. . |
| 299758 | 1/1989 | European Pat. Off. . |
| 0305175 | 3/1989 | European Pat. Off. . |
| 305175 | 3/1989 | European Pat. Off. . |
| 313071 | 4/1989 | European Pat. Off. . |
| 332344 | 9/1989 | European Pat. Off. . |
| 460322 | 12/1991 | European Pat. Off. . |
| 472362 | 2/1992 | European Pat. Off. . |
| 480379 | 4/1992 | European Pat. Off. . |
| 479245 | 4/1992 | European Pat. Off. . |
| 478150 | 4/1992 | European Pat. Off. . |

(List continued on next page.)

OTHER PUBLICATIONS

Mobay Corporation, Coatings Division publication, "Raw Materials for High Performance Coatings", 1989.
PAPI 94 Polymeric MDI, Technical Information, 1986.
Mobay Corporation, Coatings Division publication, "Product Information—DESMODUR N-3300", May 1991.
Mobay Corporation, Coatings Division publication, "Product Data—DESMODUR W", Apr. 1987.
Mobay Corporation, Coatings Division publication, "Product Information—DESMODUR H".
Olin Corporation, Urethane Chemicals, Product Data, "POLY-G 55-28", May 1988.
Olin Corporation, Urethane Chemicals, Product Data, "Poly-G 55-56", May 1988.

(List continued on next page.)

*Primary Examiner*—James J. Seidleck
*Assistant Examiner*—John M. Cooney, Jr.
*Attorney, Agent, or Firm*—Theodore R. Furman, Jr.; John M. Kilcoyne

[57] ABSTRACT

Pressure-sensitive adhesives which possess absorptivity and/or permeability properties to remove transepidermal water loss and/or other bodily fluids that come into contact with the adhesive, in combination with a fine balance of cohesion and adhesion properties, can be formulated by controlling the crosslinking of a polyurethane polymer having excess hydroxyl functionality, a glass transition temperature of less than about 0° C., a moisture absorption of at least about 20% of its weight and/or a moisture vapor transmission rate of at least about 300 grams/meter²/24 hours measured at 37° C. and a 90% relative humidity gradient. Adhesives of these polymers possess a peel adhesion to human skin of between about 0.3 and 4 newtons/cm width of the polymer or adhesive.

23 Claims, 4 Drawing Sheets

U.S. PATENT DOCUMENTS

| | | | |
|---|---|---|---|
| 4,359,558 | 11/1982 | Gould et al. | 525/454 |
| 4,374,883 | 2/1983 | Winslow | 428/40 |
| 4,408,023 | 10/1983 | Gould et al. | 525/454 |
| 4,415,628 | 11/1983 | Cioca et al. | 428/335 |
| 4,420,603 | 12/1983 | Nelb et al. | 528/80 |
| 4,424,305 | 1/1984 | Gould et al. | 525/127 |
| 4,439,583 | 3/1984 | Gould et al. | 525/127 |
| 4,439,584 | 3/1984 | Gould et al. | 525/127 |
| 4,439,585 | 3/1984 | Gould et al. | 525/127 |
| 4,451,635 | 5/1984 | Gould et al. | 528/71 |
| 4,452,845 | 6/1984 | Lloyd et al. | 428/220 |
| 4,454,309 | 6/1984 | Gould et al. | 525/454 |
| 4,460,369 | 7/1984 | Seymour | 604/897 |
| 4,475,908 | 10/1984 | Lloyd | 604/339 |
| 4,496,535 | 1/1985 | Gould et al. | 424/19 |
| 4,497,862 | 2/1985 | Cioca et al. | 428/220 |
| 4,497,914 | 2/1985 | Allen, Jr. et al. | 523/105 |
| 4,497,932 | 2/1985 | Trovati | 524/591 |
| 4,505,976 | 3/1985 | Doehnert et al. | 428/355 |
| 4,516,571 | 5/1985 | Buchan | 128/132 R |
| 4,524,104 | 6/1985 | Hagio et al. | 428/341 |
| 4,551,490 | 11/1985 | Doyle et al. | 524/22 |
| 4,561,858 | 12/1985 | Allen, Jr. et al. | 604/336 |
| 4,590,022 | 5/1986 | Cioca et al. | 264/41 |
| 4,595,001 | 6/1986 | Potter et al. | 128/156 |
| 4,623,593 | 11/1986 | Baler et al. | 428/447 |
| 4,626,475 | 12/1986 | Goel et al. | 428/423.1 |
| 4,638,043 | 1/1987 | Szycher et al. | 528/75 |
| 4,638,795 | 1/1987 | Richter et al. | 128/90 |
| 4,638,797 | 1/1987 | Merrill et al. | 128/156 |
| 4,644,018 | 2/1987 | Bowditch et al. | 521/130 |
| 4,650,705 | 3/1987 | Ghodsian | 428/40 |
| 4,657,006 | 4/1987 | Rawlings et al. | 128/156 |
| 4,661,099 | 4/1987 | von Bittera et al. | |
| 4,685,455 | 8/1987 | Vrouenraets | 128/156 |
| 4,722,946 | 2/1988 | Hostettler | 521/158 |
| 4,729,914 | 3/1988 | Kliment et al. | 428/36 |
| 4,740,534 | 4/1988 | Matsuda et al. | 523/111 |
| 4,743,673 | 5/1988 | Johnston et al. | 528/60 |
| 4,747,401 | 5/1988 | Potter et al. | 128/156 |
| 4,753,231 | 6/1988 | Lang et al. | 128/156 |
| 4,780,512 | 10/1988 | Gould et al. | 525/454 |
| 4,798,201 | 1/1989 | Rawlings et al. | 128/156 |
| 4,798,876 | 1/1989 | Gould et al. | 525/457 |
| 4,803,257 | 2/1989 | Goel | 528/45 |
| 4,806,614 | 2/1989 | Matsuda et al. | 528/59 |
| 4,826,493 | 5/1989 | Martini et al. | 604/327 |
| 4,830,855 | 5/1989 | Stewart | 424/448 |
| 4,841,962 | 6/1989 | Berg et al. | 128/156 |
| 4,871,798 | 10/1989 | Dormish et al. | 524/591 |
| 4,904,247 | 2/1990 | Therriault et al. | 604/304 |
| 4,914,173 | 4/1990 | Ansell | 528/49 |
| 4,917,929 | 4/1990 | Heinecke | 428/41 |
| 4,925,671 | 5/1990 | Abber | 424/448 |
| 4,952,618 | 8/1990 | Olsen | 524/17 |
| 4,977,892 | 12/1990 | Ewall | 128/156 |
| 4,987,186 | 1/1991 | Akiyama et al. | 525/107 |
| 4,999,407 | 3/1991 | Gilch et al. | 525/457 |
| 5,000,955 | 3/1991 | Gould et al. | 424/409 |
| 5,017,625 | 5/1991 | Ansell . | |
| 5,024,880 | 6/1991 | Veasley et al. | 428/317.5 |
| 5,036,143 | 7/1991 | Brauer et al. | 524/361 |
| 5,045,601 | 9/1991 | Capelli et al. | 525/327.1 |
| 5,059,189 | 10/1991 | Cilento et al. | 604/307 |
| 5,059,424 | 10/1991 | Cartmell et al. | 424/443 |
| 5,061,424 | 10/1991 | Karimi et al | 264/171 |
| 5,076,265 | 12/1991 | Wokalek | 128/156 |
| 5,089,364 | 2/1992 | Lee et al. | 430/58 |
| 5,157,101 | 10/1992 | Orr | 528/74.5 |
| 5,362,834 | 11/1994 | Schapel et al. . | |

FOREIGN PATENT DOCUMENTS

| | | |
|---|---|---|
| 1594164 | 7/1970 | Germany . |
| 1770425 | 2/1972 | Germany . |
| 2141805 | 2/1972 | Germany . |
| 2435217 | 2/1975 | Germany . |
| 2002457 | 3/1975 | Germany . |
| 2436873 | 2/1976 | Germany . |
| 1904102 | 6/1976 | Germany . |
| 2555866 | 6/1976 | Germany . |
| 2555836 | 6/1976 | Germany . |
| 2210286 | 12/1976 | Germany . |
| 2005694 | 1/1977 | Germany . |
| 2320197 | 9/1978 | Germany . |
| 1570468 | 1/1980 | Germany . |
| 2139640 | 11/1980 | Germany . |
| 3013214 | 10/1981 | Germany . |
| 3018131 | 11/1981 | Germany . |
| 3209374 | 11/1982 | Germany . |
| 2328430C2 | 5/1983 | Germany . |
| 2210594 | 9/1983 | Germany . |
| 3220866 | 12/1983 | Germany . |
| 3220865C2 | 8/1984 | Germany . |
| 3325735 | 1/1985 | Germany . |
| 3621885 | 1/1987 | Germany . |
| 3631397C2 | 6/1988 | Germany . |
| 3709920 | 10/1988 | Germany . |
| 3843421 | 7/1989 | Germany . |
| 57-109877 | 7/1982 | Japan . |
| 62-106978 | 5/1987 | Japan . |
| 1216672 | 12/1970 | United Kingdom . |
| 9405239 | 3/1994 | WIPO . |

OTHER PUBLICATIONS

Olin Chemicals, Product Data, "POLY–G 55–37", 1987.

Mobay Corporation, Coatings Division publication, "MATERIAL SAFETY DATA SHEET—Desmodur N–3300", Mar. 8, 1991.

Mobay Corporation, Coatings Division publication, "MATERIAL SAFETY DATA SHEET—Desmodur W", Jun. 26, 1991.

Mobay Corporation, Coatings Division publication, "MATERIAL SAFETY DATA SHEET—Desmodur H", Nov. 30, 1990.

PAPI 580 POLYMERIC MDI, Technical Information, 1986.

Olin Chemicals, PRODUCT DATA, "POLY–G 83–34", 1987.

Olin, MATERIAL SAFETY DATA, "POLY–G 55–37", Sep. 25, 1989.

Schollenberger, C. S., Handbook of Adhesives, "Polyurethane–and Isocyanate–Based Adhesives", pp. 359–380.

Shikinami et al., Kobunshi Ronbunshu, "Synthesis of Medical Adhesives from Segmented Poly(urethane)s," 49(1), 19–27, 1992.

Shikinami et al., Kobunshi Ronbunshu, "Physical Properties of Medical Adhesives from Segmented Poly(urethane)s," 48(1), 29–36, 1992.

POLYURETHANE PRESSURE-SENSITIVE ADHESIVES

This is a continuation of application Ser. No. 07/973,448 filed Nov. 9, 1992, entitled "Polyurethane Pressure-Sensitive Adhesives", which is now abandoned.

FIELD OF THE INVENTION

This invention relates to polyurethane pressure-sensitive adhesives. More particularly, this invention relates to polyurethane pressure-sensitive adhesives which exhibit a high degree of water absorption and/or high water vapor transmission capabilities so as to be especially suitable for use in a medical article for application to human skin. Another aspect of this invention relates to medical devices, including ostomy devices and wound dressings, which incorporate such polyurethane pressure-sensitive adhesives therein.

BACKGROUND OF THE INVENTION

Until the early 1950's, commonly used pressure-sensitive adhesives ("PSAs") for skin applications were based on natural or synthetic rubber compositions compounded with low molecular weight tackifiers, plasticizers, stabilizers, etc. These adhesives had the disadvantage of being quite hydrophobic and incapable of absorbing water. Thus, such adhesives would trap water under the covered area, often causing skin maceration or other skin damage. Furthermore, the low molecular weight ingredients compounded into these adhesives often would penetrate the skin, causing irritation or sensitization.

Polyacrylate PSAs are an improvement over the rubber-based adhesives, partly due to their self-adhesive property. This property allows them to be prepared as single-component polymeric materials without the need for potentially allergenic modifying or tackifying agents. However, these adhesives often contain unreacted residual acrylic monomer as an impurity in an amount which would irritate and/or sensitize skin. Although these polyacrylate PSAs are much more permeable to moisture or water vapor than are the rubber-based adhesives, they are incapable of absorbing any significant amounts of moisture or water. Therefore, when used for long duration in skin or wound care applications, adhesion is compromised and/or skin damage or maceration may result.

One variation of these polyacrylate PSAs is disclosed in U.S. Pat. No. 4,914,173 to Ansell. The specific PSAs of that patent are obtained by reacting an isocyanate prepolymer, which is the reaction product of a poly-functional isocyanate and a polyoxyalkylene diol monoalkyl ether, with a hydroxy-containing ester of acrylic or methacrylic acid to form a functionalized prepolymer and then cross-linking the polymer by irradiation to form a PSA that is not self-adherent but is capable of absorbing up to 95% by weight of water when hydrated. Although useful in applications where the adhesive will contact a moist or wet environment, these adhesives do not have sufficient tack or initial adhesive properties to be adherent to the skin for certain uses.

An advance in PSA formulation for skin and particularly for wound care applications was the development of compositions comprising blends of one or more water-soluble or swellable hydrocolloids and a tacky, viscous, polymeric material such as polyisobutylene as disclosed in Chen U.S. Pat. No. 3,339,546. Another example is Doyle et al. U.S. Pat. No. 4,551,490 which discloses medicinal grade pressure-sensitive compositions containing polyisobutylenes or blends of polyisobutylenes and butyl rubber, a styrenic radical or block type copolymer, mineral oil and water soluble hydrocolloid gum and a tackifier. Such hydrocolloid containing PSAs have the advantage of providing the desired adhesion to skin and, at the same time, are capable of absorbing transepidermal water loss (i.e., perspiration) or other body fluids, including wound exudates.

Hydrocolloid containing PSAs have found use in medical applications such as ostomy devices and wound dressings, where the adhesives maintain the device on skin for several days without skin damage. However, existing hydrocolloid PSAs have certain limitations in that they are opaque, lack quick initial tack, and tend to disintegrate upon excessive water absorption.

Polyurethanes are polymeric products of diols or polyols and diisocyanates or polyisocyanates. Despite the broad applications of polyurethane chemistry, polyurethane based PSAs are not widely used and to date have been found suitable for only a few specialized applications. A suitable balance of elastic and viscous properties which is required in a PSA has not been readily attainable in conventional polyurethane materials.

Existing polyurethane based adhesives function either as weak elastics or simply as high viscosity liquids. The adhesives composed of the elastic type polyurethanes tend to fail by gradually peeling away from surfaces to which they have been applied. The high viscosity type polyurethanes, which are typically obtained by using a substantial excess of polyol, leave a residue upon removal, and their cohesive strength is too low to withstand the stresses applied in many applications.

The difficulty of attaining this balance of viscoelastic characteristics in a polyurethane explains the paucity of prior art polyurethane PSA literature. Allen et al. U.S. Pat. No. 4,497,914 discloses an ostomy gasket adhesive comprised of a polyurethane prepared by reaction of an organic polyisocyanate with one or more di or polyfunctional hydroxyl compounds, for example, polyols derived from propylene or ethylene oxide, in which is incorporated a hydrophilic filler, such as a cellulosic or natural gum. The adhesive is capable of absorbing bodily fluids by virtue of dispersed hydrophilic filler physically encapsulated within the self-sustaining polyurethane adhesive composition.

Muller et al. U.S. Pat. No. 3,930,102 discloses the preparation of a webstock having a self-adhesive polyurethane coating produced by the reaction of a trifunctional propylene oxide based polyol and an aliphatic diisocyanate employing an NCO/OH ratio in the range of 0.71 to 0.85. This type of webstock is said to be suitable for the production of labels and tapes. However, these compositions are not sufficiently hydrophilic to allow absorption of bodily fluids.

A need thus exists for polyurethane pressure-sensitive adhesives for skin application which have adequate moisture absorption or permeation capacities and have other desired properties, such as transparency, conformability to body shape, quick tack, adhesive strength tailorable to the application, high wet strength, and lack of cold flow.

SUMMARY OF THE INVENTION

This invention relates to pressure-sensitive adhesives comprising a polyurethane polymer having excess hydroxyl functionality, a glass transition temperature of less than about 0° C., a moisture absorption at equilibrium of at least about 20% of its weight and/or a moisture vapor transmission rate of at least about 300 grams/meter$^2$/24 hours measured at 37° C. and a 90% relative humidity gradient. Advantageously, the glass transition temperature of the polymer is less than about −30° C., the moisture absorption at equilibrium of at least about 100% of its weight and/or the moisture vapor transmission rate is at least about 500 grams/meter$^2$/24 hours. These polymers provide a peel adhesion to human skin of between about 0.3 and 4 and preferably between about 0.5 and 3.5 newtons/cm width of the polymer.

Preferably, the polyurethane polymer is formed by the reaction of an isocyanate component and a polyol component at a molar ratio of isocyanate moieties to hydroxyl moieties of less than one with at least one of the components having a functionality that is greater than two to facilitate crosslinking. The polymer is crosslinked to a crosslink density alpha ($\alpha$) defined by the equation $$\alpha \approx \frac{\sum_{i=1}^{i=1} X_i(F_i - 2)}{(1.05 - r)Mw}$$

wherein i=1 to n where n is the number of the reactant components $X_i$=mole fraction of i$^{th}$ component $F_i$=functionality of the i$^{th}$ component r=the NCO/OH molar ratio Mw=Molecular weight of the polyol of between about $10^{-4}$ and $10^{-3}$ to obtain the desired properties. When the isocyanate component is an aliphatic polyisocyanate, the crosslink density is preferably between about $2 \times 10^{-4}$ and $10^{-3}$, while for aromatic polyisocyanates the crosslink density is preferably between about $4 \times 10^{-4}$ and $9 \times 10^{-4}$.

A preferred molar ratio is between about 0.5 and 0.99, and more preferably between about 0.65 and 0.9. The polyol component advantageously comprises a polyether polyol having a molecular weight of between about 1000 and 10,000, such as a homopolymer or copolymer containing ethylene oxide or propylene oxide groups. The polyol component may also be a hydroxyl terminated prepolymer. When moisture absorbent adhesives are desired, the polyol component can be a polyether diol or triol containing at least about 30% by weight of ethylene oxide groups.

The isocyanate component has a functionality of equal to or greater than 2, and may be an aliphatic polyisocyanate, an aromatic polyisocyanate or combinations thereof. Also, the isocyanate component may be an isocyanate terminated prepolymer. As noted, at least one of the isocyanate or polyol components must have a functionality of greater than 2 to obtain the desired crosslinking of the polymer.

The invention also relates to a medical article or device for application to skin which comprises a layer of the pressure-sensitive adhesive described above and a backing material in contact with at least a portion of one side of the layer. The backing material may be a natural or synthetic fiber, a woven or non-woven fabric, paper or a thermoplastic polymer. Also, a release layer in contact with the side of the pressure-sensitive adhesive layer opposite the backing material may be included to protect the adhesive prior to use. Thus, the release layer comprises a material that does not permanently bond to the pressure-sensitive adhesive layer, such as a silicone coating.

This medical article may also include a backing layer and a layer of the pressure-sensitive adhesive described above on at least a portion of one side of the backing layer for contacting the skin and securing the article thereto. This article advantageously includes a moisture or water absorbent material positioned for placement upon a moist or wet environment, wherein the pressure-sensitive adhesive layer is located adjacent at least a portion of the absorbent material. If the absorbent material is in the form of a disk, the pressure-sensitive material layer may be associated with and at least partially surround the perimeter of the disk. A support layer may be provided for the absorbent material, such that the pressure-sensitive adhesive layer is attached onto at least a portion of the periphery of the support layer and surrounds the entire perimeter of the disk.

In another embodiment, the medical article further comprises an attachment member for connection to another medical device, such as a bag or container. Thus, the disk would include an aperture therein to permit passage of a fluid therethrough. To provide a secure attachment to the patient and to prevent leakage, means for joining the pressure-sensitive adhesive layer to the support layer may be used, such as an ultrasonic weld.

Accordingly, the medical article or device of the invention may be provided in the form of an ostomy device, a wound dressing, a medical tape, a bandage, an incontinence device, a dermatological device, a transdermal device, a surgical incise drape or an intravenous catheter securement device.

Another embodiment of the invention relates to a method for making a pressure-sensitive adhesive for application to skin which comprises providing a mixture of an isocyanate component and a polyol component at a molar ratio of isocyanate moieties to hydroxyl moieties of less than one; selecting at least one of the components to have a functionality that is greater than two to facilitate crosslinking; and reacting the isocyanate and polyol components in the presence of a catalyst to form a polyurethane polymer having a glass transition temperature of less than about 0° C., a moisture absorption at equilibrium of at least about 20% of its weight and/or a vapor transmission rate of at least about 300 grams/meter$^2$/24 hours measured at 37° C. and a 90% relative humidity gradient.

The mixture may be cast upon a substrate and heated at a sufficient temperature of between about 100° and 150° C. and for a sufficient time of between about 1 to 25 minutes to form a layer of the polymer. This layer may be provided upon a backing material or a release layer and would possess a peel adhesion to human skin of between about 0.3 and 4 and preferably between about 0.5 and 3.5 newtons/cm width of the polymer.

DETAILED DESCRIPTION OF THE INVENTION

The invention provides polyurethane pressure-sensitive adhesive compositions and medical articles or devices incorporating such adhesives. These adhesives are particularly useful in applications requiring contact with the skin. They thus may be used as adhesives for ostomy care and incontinence appliances, bandages, drug delivery systems, and other devices which are intended to be attached to the skin.

It has been discovered that polyurethane pressure-sensitive adhesives suitable for medical use should possess two distinct characteristics. One characteristic is their absorptivity and/or permeability to remove from the application site transepidermal water loss and/or other bodily fluids that come into contact with the adhesive. The other characteristic is a fine balance of cohesion and adhesion of the polyurethane. It was also discovered that this balance of cohesion and adhesion can be obtained by controlling the crosslinking of the polymer within well defined limits.

The polyurethane is prepared by reacting a polyol having a molecular weight of from about 1,000 to about 10,000 or mixtures of such polyols, with an isocyanate such as a polyisocyanate. Although any of a wide variety of polyols can be used, those which are not crystalline are the most suitable. Exemplary polyols include polyether diols or triols (ethylene oxide and propylene oxide polymers and copolymers) such as those available from Olin (e.g., the Poly G series). In general, for comparable formulations, the higher molecular weight polyols would provide greater peel strengths in the resulting adhesive.

Where increased moisture or water absorption properties are desired in the PSA, polyols that contain a significant amount of polyoxyethylene are used so as to increase the hydrophilic character of the polymer. These polyols should contain at least about 30% of polyoxyethylene in order to enable the polymer to absorb water in an amount of at least about 20% of its weight and as high as 400 to 1000%.

Typical polyols which are useful for this embodiment include Dow Chemical's XUS15176 and the various commercial Carbowaxes which are available in a range of molecular weights from the Union Carbide Corporation. Representative Carbowaxes are PEG (Carbowax 1450) and PEG (Carbowax 8000) in which the numbers refer to molecular weights. The proportion of polyoxyethylene which is present in the polyol will determine the degree of hydrophilic character of the polyurethane. Increasing the amount of polyoxyethylene promotes strong hydrophilic properties to the final product, while a lessened hydrophilic character results by increasing the proportion of polyoxypropylene in the polyol.

The functionality of the polyol that is used is at least 2 and usually is greater than 2, with the higher functionalities providing increased crosslinking of the polyurethane. A number of polyols which are suitable when used alone or in combination are listed below in Table I.

The isocyanates which may be used in making the polyurethanes of the PSAs of the invention may be represented by R(NCO)n wherein n is at least 2 and preferably between about 2 and 4, and R is an aliphatic, alicyclic, aliphatic-alicyclic, aromatic, or aliphatic-aromatic hydrocarbon compound ranging from about 4 to 26 carbon atoms, but more conventionally from about 6 to 20 and generally from about 6 to 13 carbon atoms.

TABLE 1

SUITABLE POLYOLS

| COMPONENT: | FUNCTIONALITY | EQUIVALENT | ETO % | SUPPLIER |
| --- | --- | --- | --- | --- |
| POLY G | | | | |
| 55-28 | 2 | 2025.00 | 30 | OLIN |
| 55-37 | 2 | 1512.00 | 30 | OLIN |
| 55-56 | 2 | 976.00 | 45 | OLIN |
| 76-120 | 3 | 457.00 | 30 | OLIN |
| 83-34 | 3 | 1576.00 | 70 | OLIN |
| 85-28 | 3 | 2025.00 | 10 | OLIN |
| 85-36 | 3 | 1508.00 | 17 | OLIN |
| VORANOL | | | | |
| 5148 | 3 | 2357.00 | 19 | DOW |
| 5287 | 2 | 1018.00 | 12 | DOW |
| 5471 | 3 | 1603.00 | 14 | DOW |
| VORAN | | | | |
| 220-037 | 2 | 1500.00 | 0 | DOW |
| 232-034 | 3 | 1636.00 | 14 | DOW |
| 240-446 | 4.5 | 125.10 | 0 | DOW |
| 240-800 | 4 | 69.70 | 0 | DOW |
| 270-370 | 7 | 155.90 | 0 | DOW |
| XUS 15176.00 | 2 | 1500.00 | 30 | DOW |
| MULTRANOL 3400 | 3 | 1000.00 | 0 | MOBAY |
| MULTRANOL 3901 | 3 | 1997.00 | 0 | MOBAY |
| MULTRANOL 9133 | 3 | 53.95 | 0 | MOBAY |
| DESMOFEN 2500 | 2 | 505.00 | 0 | MOBAY |
| QUADROL | 4 | 73.00 | 0 | MOBAY |
| CARBOWAX | | | | |
| 1450 | 2 | 714.00 | 100 | CARBIDE |
| 3350 | 2 | 1638.00 | 100 | CARBIDE |
| 4600 | 2 | 2352.00 | 100 | CARBIDE |
| 8000 | 2 | 4141.00 | 100 | CARBIDE |
| TERATHANE | | | | |
| 1000 | 2 | 500 | 0 | DUPONT |
| 2000 | 2 | 1024.00 | 0 | DUPONT |
| PLURACOL 380 | 3 | 2235.00 | 0 | BASF |
| POLY THF ER 1250 | 2 | 625 | 0 | BASF |
| FOMREZ | | | | |
| EPD-56 | 2 | 1041.00 | 45 | WITCO |
| EPD-28 | 2 | 2086.00 | 45 | WITCO |
| K22-170 | 6 | 308.00 | 90 | WITCO |
| L49-28 | 3 | 1990.00 | 25 | WITCO |
| ECFL10007 | 3 | 278.00 | 90 | WITCO |
| WITCONL PEG1000L | 2 | 505.00 | 90 | WITCO |

TABLE 2

SUITABLE ISOCYANATES

| COMPONENT: | FUNCTIONALITY | EQUIVALENT | SUPPLIER |
| --- | --- | --- | --- |
| PAPI 94 | 2.2 | 131.50 | DOW |
| PAPI 2580 | 3 | 139.60 | DOW |
| ISONATE 2181 | 2 | 182.60 | DOW |
| ISONATE 2125M | 2 | 125.50 | DOW |
| MONDUR MR | 2.7 | 131.00 | MOBAY |
| MONDUR CD | 2 | 143.00 | MOBAY |
| MONDUR CB75 | 3 | 323.00 | MOBAY |
| DSMODUR W | 2 | 132.00 | MOBAY |
| TMXDI | 2 | 122.10 | CYANAMID |
| CYTHANE 3160 | 3 | 404.00 | CYANAMID |
| TDI 80 | 2 | 87.00 | OLIN |
| DMI 1410 | 2 | 295.77 | HENKEL |

Representative examples of diisocyanates include aliphatic isocyanates such as tetramethylene diisocyanate; hexamethylene diisocyanate; trimethylhexamethylene diisocyanate; dimer acid diisocyanate; isophorone diisocyanate; diethylbenzene diisocyanate; decamethylene 1,10-diisocyanate; cyclohexylene 1,2-diisocyanate and cylohexylene-1,4-diisocyanate and the aromatic isocyanates such as 2,4- and 2,6-tolylene diisocyanate; 4,4-diphenylmethane diisocyanate; 1,4-naphthalene diisocyanate; dianisidine diisocyanate; toluidine diisocyanate; m-xylylene diisocyanate; tetrahydronaphthalene-1,5-diisocyanate; and bis(4-isocyanatophenyl)methane.

Polymeric polyisocyanates having a functionality of greater than 2, such as neopentyl tetraisocyanate, can also be used. A number of suitable isocyanates are listed in Table 2 below. In addition, mixtures of di- and tri-functional isocyanates are commercially available and may be used to obtain an isocyanate components having a functionality of between 2 and 3, while mixtures of tri- and tetra-functional isocyanates may be used to obtain functionalities of between 3 and 4 (i.e., DESMODUR N 3300 from Miles, Perkasie, Pa.). These tri- and tetra-functional isocyanates are illustrated below.

Desmodur N 3300 has a functionality of about 3.4–3.6 and it is a mixture of the two isocyanates depicted above. This isocyanate compound is preferred from the standpoint of toxicity because it is an aliphatic isocyanate derivative that produces a non-toxic degradation product. Furthermore, the isocyanate compounds shown above can be mixed together or with the diisocyanates mentioned above to attain the desired functionality of the isocyanate component.

Generally speaking, the polyurethane is prepared from about 75% to 95% of the polyol, and about 5% to 25% of the polyisocyanate. The relative amounts are selected so that the NCO/OH ratio is between about 0.5 and 0.99 and preferably between about 0.65 to 0.9, so that these polyurethanes have excess hydroxyl functionality.

In preparing the polyether polyurethane adhesives of this invention, the polyols and the polyisocyanates are reacted in the presence of known catalysts for such reaction, for example, tin salts and organic tin esters such as dibutyltin dilaurate and stannous octoate. An advantageous catalyst is METACURE T-12 by Air Products and Chemicals, Inc., because this catalyst has been approved by the FDA for medical applications and provides a satisfactory reaction.

The adhesive is prepared by first casting a mixture of the isocyanates, polyols, and catalyst onto the desired substrate and curing it by heating at about 100°–150° C. for about 1–25 and preferably about 3–10 minutes. It is also possible to initially form an isocyanate terminated prepolymer from a portion of the polyol and the isocyanate, and then to react that prepolymer with the balance of the polyol. As noted above, there is a greater equivalent weight of polyol compared to isocyanate, such that the final polymer is, in effect, a polyol terminated polyurethane polymer.

Also, it is preferred for the pressure-sensitive adhesive to have a glass transition temperature (Tg) of less than 0° C. and preferably less than −30° C. Thus, the amount of crystalline polyol used, if any, should be held to a minimum. By choosing polyols which are not crystalline or do not crystallize, or which do not cause phase separation during reaction, a transparent, uncolored polymer is obtained. A colored polymer is also avoided by selecting isocyanate and polyol components which form polymerization products that do not contain multiple bonds which would be capable of absorbing light or heat energy and undergo transformations resulting in colors.

The pressure-sensitive polyurethane adhesives of this invention each have an MVTR (at equilibrium) of at least 300 and preferably greater than 500 g/m$^2$/day when measured at 37° C. and a 90% relative humidity gradient. When these adhesives are applied onto skin, the skin can "breathe", such that any excess moisture generated by perspiration of the skin can pass through the adhesive to prevent deterioration of the skin, while some moisture is retained to provide an environment which promotes healing.

For applications where the PSAs encounter a highly moist or wet environment, the PSA can be formulated to absorb more than 20% of water based on the weight of the adhesive in addition to providing the desired MVTR. These adhesives are formulated with polyols that contain a significant amount of polyoxyethylene so as to increase the hydrophilic character of the polymer. The Carbowax polyols mentioned above are available with as high as 70% by weight of polyoxyethylene and can be used to provide the desired water absorption properties of the polymer. These water absorptive adhesives contain all of the required properties of the PSAs previously described.

Another feature of the pressure-sensitive adhesives of the present invention is that the amount of leachables is relatively low. Gel chromatography studies show that unreacted polyols are the only components in the extracted media. In addition, the amount of leachables can be controlled by the molar ratio of the components used to form the polymer, the degree of crosslinking of the polymer and the chemistry of the polyol components.

A quantitative measure of the pressure-sensitive adhesive characteristics of a material is its peel strength to a desired substrate. Although the desired substrate for a medical adhesive is living human skin, peel adhesion is more conveniently measured on a standard substrate, namely a stainless steel test panel for quality control purposes. These test values can be correlated to those which are desired for adhesion to human skin. As noted above, peel strength to human skin for polyurethane adhesives for medical uses range from about 0.3 to 4 newtons/cm. width of the adhesive, depending upon the backing and the stresses the adhesive is expected to encounter during its use, and preferably between about 0.5 and 3.5 newtons/cm. width for adhesion to human skin.

It has been discovered that the polyurethane adhesive peel strength, for a given backing and at a given adhesive thickness, is a function of the extent of crosslinking which, in turn, depends upon the functionality of the components used to form the polyurethane polymer. The extent of crosslinking can be expressed as the number of crosslinks per unit weight. With a greater extent of crosslinking, the peel adhesion becomes lower, such that peel adhesion has been found to be inversely related to the extent of crosslinking.

It has further been found that this crosslink density is a function of an interplay of molecular parameters of the polyurethane components. A mathematical relationship incorporating these components has been derived to define the optimum combination of the kind and proportions of the components which results in the formation of polyurethane PSAs for the specified medical uses. This relationship can be used to calculate a value, designated as $\alpha$, which is representative of the extent of crosslinking of the polymer. Thus, the $\alpha$ value, which is based on the average functionality of the reactants, the NCO/OH mole ratio, and the molecular weight of the polyol, may be used as a measure of the performance of one polymer relative to another, as well as to select which polymers are useful in accordance with the teachings of the present invention.

The following expression sets forth the relationship between the variables which is used to calculate $\alpha$. As noted above, the peel strength is inversely proportional to the extent of crosslinking, which can be expressed as follows:

$$\text{Desired Peel Strength} = \frac{K}{\text{number of crosslinks/unit weight of polymer}}$$

wherein the number of crosslinks/unit weight of polymer is proportional to $\alpha$ as calculated by the following formula: wherein $$\alpha \approx \frac{\sum_{n}^{i=1} X_i(F_i - 2)}{(1.05 - r)Mw}$$

i=1 to n where n is the number of the reactant components $X_i$=mole fraction of $i^{th}$ component $F_i$=functionality of the $i^{th}$ component r=the NCO/OH molar ratio Mw=Molecular weight of the polyol.

Figure 1:
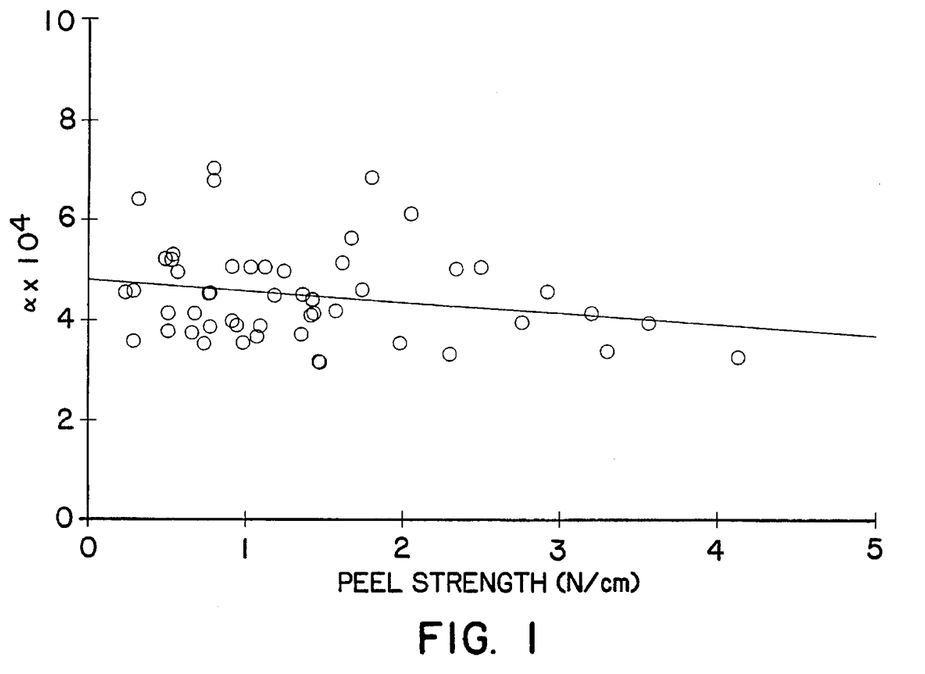
FIG. 1 is a graph showing the effect of the $\alpha$ value on peel strength of pressure-sensitive polyurethane adhesives made from aliphatic diisocyanates.
Figure 2:
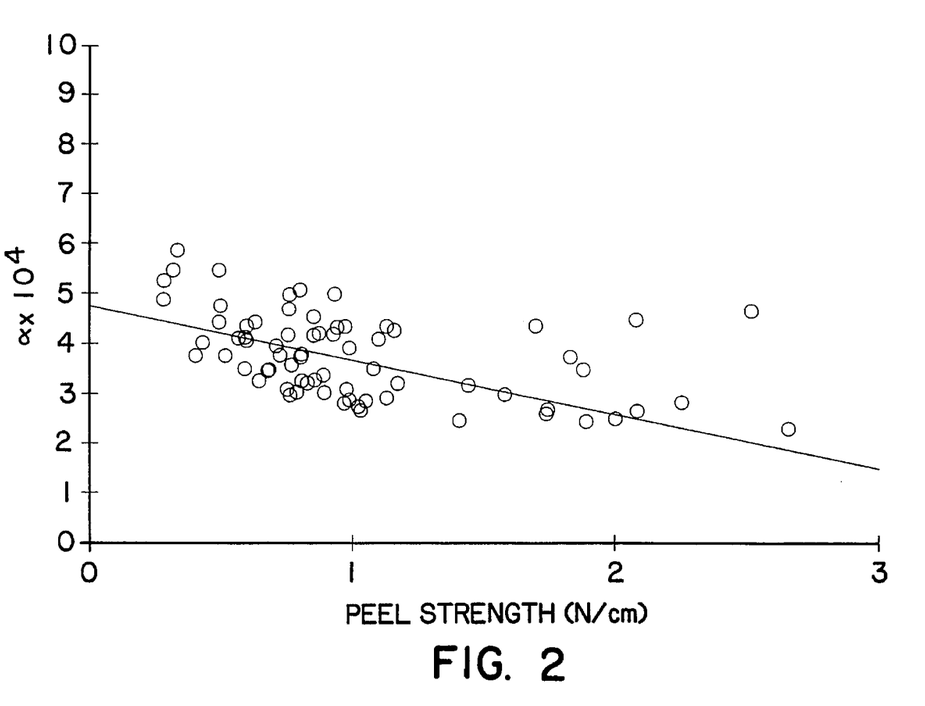
FIG. 2 is a graph showing the effect of the $\alpha$ value on peel strength of pressure-sensitive polyurethane adhesives made from aromatic diisocyanates.

Thus, in a given polyurethane formulation, an interplay of different parameters governs the peel strength of the adhesive. Interdependence of these parameters, and its conformance to the above equation was demonstrated by plotting the $\alpha$ value for a large number of polyurethane adhesive formulations against their peel strength, as shown in FIGS. 1 and 2. The supporting data for these figures are set forth in Tables 3 and 4.

An $\alpha$ value in the range of $10^{-4}$ to $10^{-3}$ is representative of an adhesive which has the desired balance of cohesive and adhesive characteristics which are typically required for a pressure-sensitive adhesive, with $\alpha$ values of between $2 \times 10^{-4}$ and $10^{-3}$ for aliphatic polyurethanes and between 4 and $9 \times 10^{-4}$ for aromatic polyurethanes being particularly advantageous.

Accordingly, based upon this information, one skilled in the art can routinely select the particular isocyanate and polyol components and molar ratios thereof to obtain polyurethane polymers which have $\alpha$ values which fall in the desired ranges. In addition, the $\alpha$ value can be calculated prior to actual formulation of the polymer, so that the experimental work is necessary only after selecting those components and molar ratios which provide $\alpha$ values in the desired range.

One can determine mathematically whether any specific combination of components used to form a polymer would have the desired properties and, if not, how to modify the polymer to either increase or decrease the $\alpha$ value to achieve the desired result.

TABLE 3

POLYURETHANE FORMULATIONS BASED ON AROMATIC ISOCYANATES

| POLYOL | | | | | DIISOCYANATE | | PROPERTIES | | | |
|---|---|---|---|---|---|---|---|---|---|---|
| XUS 15176 | POLY G-55-28 | POLY G-55-56 | POLY G-83-34 | DEG | ISON 2181 | PAPI 2580 | NCO/OH Ratio | BALL cm | PEEL N/cm | WATER UPTAKE % |
| | 27.37 | 19.90 | 42.47 | 1.42 | | 8.84 | 0.722 | 1.00 | 0.73 | 429 |
| | 30.84 | 29.76 | 23.90 | 3.23 | | 12.28 | 0.723 | 0.88 | 2.53 | 398 |
| | 30.53 | 29.76 | 23.94 | 3.22 | | 12.26 | 0.723 | 0.80 | 1.46 | 360 |
| | 21.63 | 33.10 | 34.98 | 1.17 | | 9.11 | 0.735 | 1.00 | 0.50 | 363 |
| | 21.47 | 33.13 | 35.06 | 1.22 | | 9.12 | 0.728 | 0.63 | 1.07 | 349 |
| | 21.01 | 34.05 | 34.58 | 1.15 | | 9.20 | 0.741 | 1.05 | 0.77 | 309 |
| | 21.87 | 34.68 | 36.66 | | | 6.84 | 0.704 | 1.20 | 0.65 | 389 |
| | | 34.92 | 55.89 | | | 9.20 | 0.925 | 1.07 | 0.48 | 268 |
| | | 41.22 | 43.51 | 2.91 | | 12.35 | 0.709 | 1.10 | 0.98 | 431 |
| | | 41.82 | 50.61 | | | 7.58 | 0.724 | 0.90 | 0.23 | 456 |
| | | 41.82 | 50.61 | | | 7.58 | 0.724 | 0.80 | 0.22 | 452 |
| | | 41.82 | 50.61 | | | 7.58 | 0.724 | 1.10 | 0.27 | 443 |
| | | 41.82 | 50.61 | | | 7.57 | 0.723 | 0.73 | 0.76 | 554 |
| | | 41.83 | 50.63 | | | 7.54 | 0.720 | 0.45 | 1.18 | 513 |
| | | 42.14 | 45.14 | 1.52 | | 11.20 | 0.798 | 0.60 | 0.53 | 474 |
| | | 42.52 | 45.70 | 1.54 | | 10.24 | 0.722 | 0.52 | 2.76 | 550 |
| | | 42.52 | 45.70 | 1.24 | | 10.24 | 0.722 | 0.78 | 1.40 | 594 |
| | | 42.53 | 45.67 | 1.54 | | 10.26 | 0.724 | 0.50 | 0.91 | 685 |
| | | 42.63 | 45.85 | 1.54 | | 9.98 | 0.703 | 0.40 | 1.35 | 751 |
| | | 42.75 | 45.88 | 1.57 | | 10.30 | 0.724 | 0.90 | 3.56 | 429 |
| | | 50.35 | 40.51 | | | 9.15 | 0.848 | 0.63 | 0.79 | 507 |
| | | 50.63 | 41.15 | | | 8.23 | 0.756 | 0.55 | 0.56 | 465 |
| | | 50.96 | 41.04 | | | 8.00 | 0.732 | 0.50 | 0.77 | 582 |
| | | 50.97 | 41.05 | | | 7.98 | 0.730 | 0.60 | 1.36 | 580 |
| | | 51.10 | 41.17 | | | 7.73 | 0.705 | 0.07 | 0.67 | 658 |
| | | 51.10 | 41.17 | | | 7.73 | 0.705 | 0.65 | 1.64 | 480 |
| | | 51.11 | 41.17 | | | 7.72 | 0.705 | 0.50 | 0.50 | 654 |

TABLE 3-continued

| POLYURETHANE FORMULATIONS BASED ON AROMATIC ISOCYANATES | | | | | | | | | | |
|---|---|---|---|---|---|---|---|---|---|---|
| POLYOL | | | | | DIISOCYANATE | | PROPERTIES | | | |
| XUS 15176 | POLY G-55-28 | POLY G-55-56 | POLY G-83-34 | DEG | ISON 2181 | PAPI 2580 | NCO/OH Ratio | BALL cm | PEEL N/cm | WATER UPTAKE % |
| | | 51.11 | 41.16 | | | 7.73 | 0.705 | 0.59 | 1.43 | 671 |
| | | 51.23 | 41.25 | | | 7.53 | 0.685 | 0.40 | 1.09 | 847 |
| | | 70.13 | 15.06 | 2.17 | | 12.63 | 0.740 | 0.48 | 1.42 | 328 |
| | | 83.39 | | 2.26 | | 14.35 | 0.802 | 0.70 | 0.31 | 194 |
| | | 83.83 | | 2.27 | | 13.90 | 0.774 | 0.50 | 1.67 | 283 |
| | | 89.44 | | | | 10.56 | 0.826 | 0.70 | 0.79 | 209 |
| | | 89.76 | | | | 10.24 | 0.798 | 1.00 | 2.05 | 293 |
| | | 90.16 | | | | 9.84 | 0.763 | 0.60 | 0.48 | 266 |
| | | 90.18 | | | | 9.82 | 0.762 | 0.77 | 0.52 | 271 |
| | | 90.20 | | | | 9.80 | 0.759 | 0.53 | 1.61 | 360 |
| | | 90.25 | | | | 9.75 | 0.755 | 0.66 | 2.50 | 282 |
| | | 90.26 | | | | 9.74 | 0.755 | 0.50 | 1.12 | 359 |
| | | 90.26 | | | | 9.74 | 0.754 | 0.40 | 1.07 | 361 |
| | | 90.27 | | | | 9.73 | 0.754 | 0.45 | 2.34 | 268 |
| | | 90.32 | | | | 9.75 | 0.755 | 0.50 | 1.03 | 344 |
| | | 90.41 | | | | 9.71 | 0.752 | 0.38 | 1.24 | 293 |
| | | 90.51 | | | | 9.49 | 0.733 | 0.40 | 1.74 | 443 |
| | | 90.65 | | | | 9.35 | 0.721 | 0.40 | 1.42 | 351 |
| 71.38 | | | 21.70 | | | 6.93 | 0.809 | 0.78 | 0.91 | 180 |
| 69.02 | | | 24.29 | | 2.02 | 4.67 | 0.724 | 0.50 | 2.07 | 360 |
| | 67.18 | | 26.63 | | | 6.19 | 0.886 | 0.60 | 1.03 | 289 |
| | 47.26 | 47.14 | | | | 5.59 | 0.752 | 0.70 | 0.28 | 298 |
| | 47.35 | 47.41 | | | | 5.24 | 0.702 | 0.70 | 0.94 | 355 |
| | 47.51 | 47.51 | | | | 5.00 | 0.668 | 0.70 | 1.98 | 414 |
| | 47.71 | 47.61 | | | | 4.79 | 0.639 | 0.40 | 4.13 | 364 |
| | | | 91.78 | 0.82 | | 7.40 | 0.720 | 0.90 | 0.44 | 615 |
| | | | 91.94 | | 8.06 | | 0.756 | 2.20 | 0.28 | 571 |

TABLE 4

| Polyurethane Formulations Based On Aliphatic Isocyanates | | | | | |
|---|---|---|---|---|---|
| POLY G-55-37 Polyol (wt %) | DESMODUR N-3300 Polyisocyanate (wt %) | DESMODUR H Diisocyanate (wt %) | NCO/OH Ratio | Peel Strength (N/cm) | Water Uptake (%) |
| 92.387 | 5.464 | 2.150 | 0.88 | 0.278 | 112.8238 |
| 92.200 | 5.808 | 1.992 | 0.88 | 0.280 | 107.9190 |
| 92.292 | 5.458 | 2.250 | 0.90 | 0.314 | 117.7052 |
| 92.106 | 5.802 | 2.092 | 0.90 | 0.331 | 108.7643 |
| 92.578 | 5.832 | 1.590 | 0.80 | 0.400 | 137.7215 |
| 92.483 | 5.826 | 1.691 | 0.82 | 0.426 | 132.7077 |
| 92.481 | 5.469 | 2.050 | 0.86 | 0.491 | 114.4501 |
| 92.294 | 5.814 | 1.892 | 0.86 | 0.496 | 116.5878 |
| 92.671 | 5.480 | 1.849 | 0.82 | 0.514 | 142.0639 |
| 92.669 | 5.123 | 2.208 | 0.86 | 0.564 | 126.2756 |
| 92.767 | 5.486 | 1.747 | 0.80 | 0.589 | 140.8154 |
| 92.388 | 5.820 | 1.792 | 0.84 | 0.595 | 126.4657 |
| 92.576 | 5.475 | 1.949 | 0.84 | 0.596 | 123.5098 |
| 92.794 | 4.533 | 2.673 | 0.90 | 0.629 | 95.4500 |
| 92.771 | 5.842 | 1.387 | 0.76 | 0.643 | 159.5735 |
| 92.676 | 5.836 | 1.487 | 0.78 | 0.676 | 155.8120 |
| 92.860 | 5.133 | 2.007 | 0.82 | 0.682 | 150.7584 |
| 92.889 | 4.538 | 2.573 | 0.88 | 0.708 | 119.9588 |
| 92.765 | 5.128 | 2.107 | 0.84 | 0.723 | 149.9817 |
| 92.866 | 5.848 | 1.286 | 0.74 | 0.750 | 197.1354 |
| 92.920 | 4.300 | 2.780 | 0.90 | 0.755 | 123.6279 |
| 92.667 | 4.765 | 2.567 | 0.90 | 0.757 | 126.4355 |
| 93.054 | 5.144 | 1.803 | 0.78 | 0.761 | 172.0021 |
| 92.985 | 4.542 | 2.472 | 0.86 | 0.767 | 154.2247 |
| 92.958 | 5.496 | 1.545 | 0.76 | 0.787 | 176.4395 |
| 92.479 | 5.112 | 2.408 | 0.90 | 0.799 | 118.0265 |
| 93.016 | 4.304 | 2.680 | 0.88 | 0.801 | 122.3668 |
| 92.858 | 4.775 | 2.367 | 0.86 | 0.805 | 132.7454 |
| 92.956 | 5.139 | 1.906 | 0.80 | 0.805 | 172.8320 |
| 92.863 | 5.491 | 1.646 | 0.78 | 0.827 | 180.9655 |
| 92.574 | 5.118 | 2.308 | 0.88 | 0.850 | 127.9587 |
| 93.081 | 4.547 | 2.372 | 0.84 | 0.853 | 201.9966 |
| 93.112 | 4.309 | 2.579 | 0.86 | 0.886 | 148.8468 |

TABLE 4-continued

| Polyurethane Formulations Based On Aliphatic Isocyanates | | | | | |
|---|---|---|---|---|---|
| POLY G-55-37 Polyol (wt %) | DESMODUR N-3300 Polyisocyanate (wt %) | DESMODUR H Diisocyanate (wt %) | NCO/OH Ratio | Peel Strength (N/cm) | Water Uptake (%) |
| 93.177 | 4.552 | 2.271 | 0.82 | 0.890 | 236.1296 |
| 92.763 | 4.770 | 2.467 | 0.88 | 0.925 | 137.7454 |
| 93.149 | 5.149 | 1.702 | 0.76 | 0.967 | 225.9732 |
| 93.208 | 4.313 | 2.478 | 0.84 | 0.976 | 172.7290 |
| 93.047 | 4.066 | 2.887 | 0.90 | 0.986 | 129.7297 |
| 93.054 | 5.502 | 1.445 | 0.74 | 0.987 | 210.3826 |
| 93.244 | 4.793 | 1.963 | 0.78 | 1.021 | 187.2292 |
| 93.244 | 5.154 | 1.601 | 0.74 | 1.031 | 242.3910 |
| 93.305 | 4.318 | 2.378 | 0.82 | 1.050 | 192.0912 |
| 93.143 | 4.070 | 2.786 | 0.88 | 1.080 | 143.0732 |
| 93.336 | 4.079 | 2.585 | 0.84 | 1.131 | 168.0455 |
| 93.050 | 4.785 | 2.165 | 0.82 | 1.173 | 192.9631 |
| 93.436 | 4.785 | 1.779 | 0.74 | 1.409 | 294.2116 |
| 93.239 | 4.075 | 2.686 | 0.86 | 1.444 | 209.9978 |
| 93.146 | 4.790 | 2.064 | 0.80 | 1.582 | 255.5226 |
| 93.371 | 4.561 | 2.068 | 0.78 | 1.740 | 241.6005 |
| 93.433 | 4.083 | 2.484 | 0.82 | 1.744 | 223.8497 |
| 92.954 | 4.780 | 2.266 | 0.84 | 1.880 | 161.5703 |
| 93.499 | 4.327 | 2.174 | 0.78 | 1.891 | 310.0115 |
| 93.529 | 4.087 | 2.383 | 0.80 | 2.001 | 242.7349 |
| 93.401 | 4.322 | 2.277 | 0.80 | 2.083 | 243.5749 |
| 93.273 | 4.556 | 2.170 | 0.80 | 2.252 | 274.8556 |
| 93.626 | 4.091 | 2.282 | 0.78 | 2.659 | 258.3830 |

The pressure-sensitive adhesive products of this invention are prepared by coating a mixture of the polyurethane adhesive components on a backing material and allowing the polyurethane components to cure. Useful backing materials are thermoplastic elastomers such as polyurethane film, plasticized PVC, breathable woven or non-woven fabrics made of natural or synthetic fibers such as polyester and porous paper. The adhesive components can also be applied to a release liner such as mylar film with a silicone coating and silicone coated paper and then after curing removed and placed on a backing material. The thickness of the adhesive coating is about 1 to 60 mils depending upon the requirements of the specific product application, while the backing material has a thickness in the range of between about 0.5 and 5 mils and typically about 1–2 mils.

The above-described polyurethane pressure-sensitive adhesives are particularly useful for attaching medical devices and other materials to the skin. The adhesives can be used as or applied to bandages, ostomy devices, incontinence devices, incise drapes, intravenous catheter holders, transdermal drug delivery devices and medical tapes such as wound closure tapes. Where absorbent adhesives are desired, such as in wound dressings, the polymers that have high water absorption properties can be successfully used. Because of the skin adhesion properties of these PSAs, i.e., no skin irritation or sensitization, and lack of skin or hair adhesion on removal, these adhesives are skin friendly and are very useful in the medical field where skin contact is required.

Figure 4:
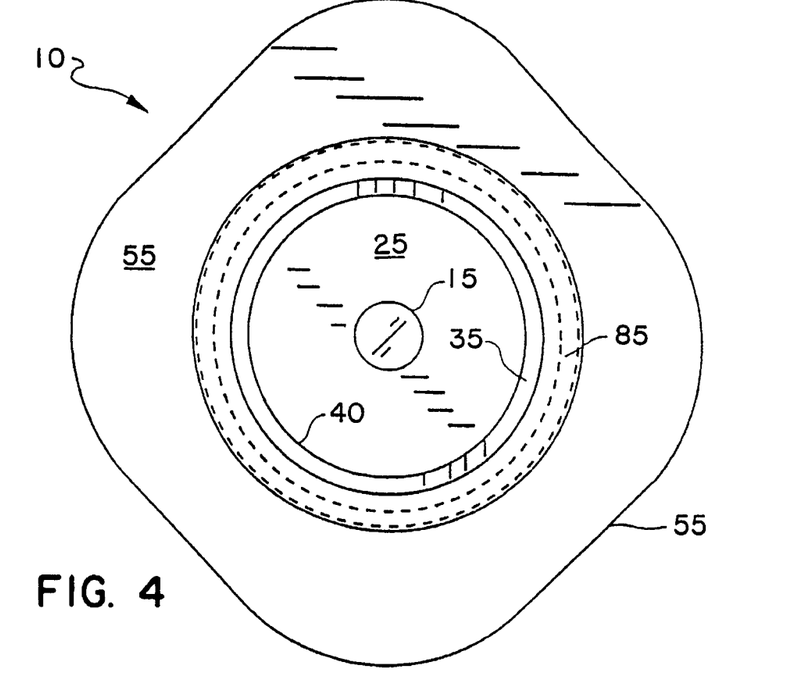
FIG. 4 is a front view of an ostomy gasket which includes a PSA band in accordance with the invention.
Figure 5:
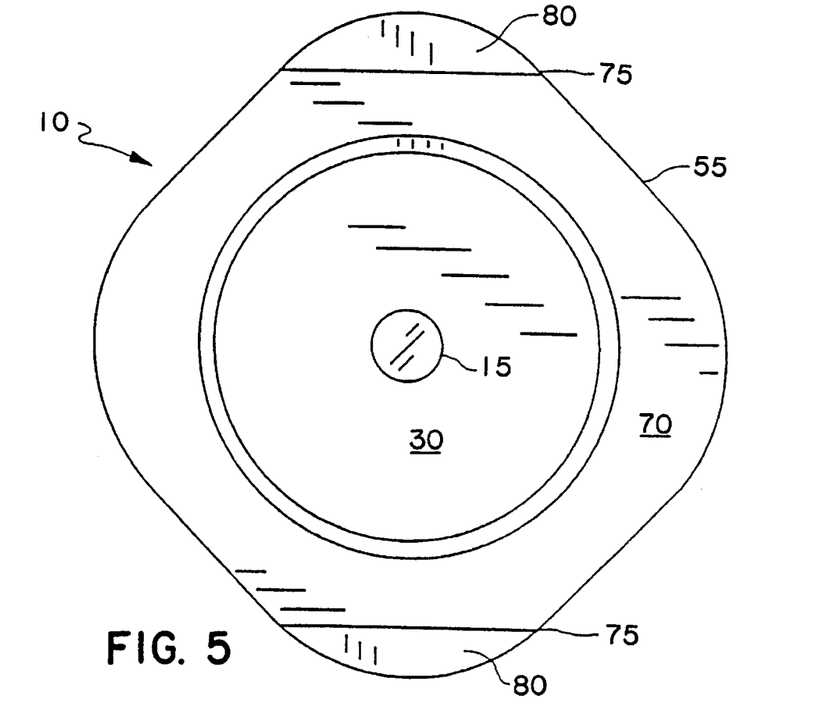
FIG. 5 is a rear view of the gasket of FIG. 4.
Figure 6:
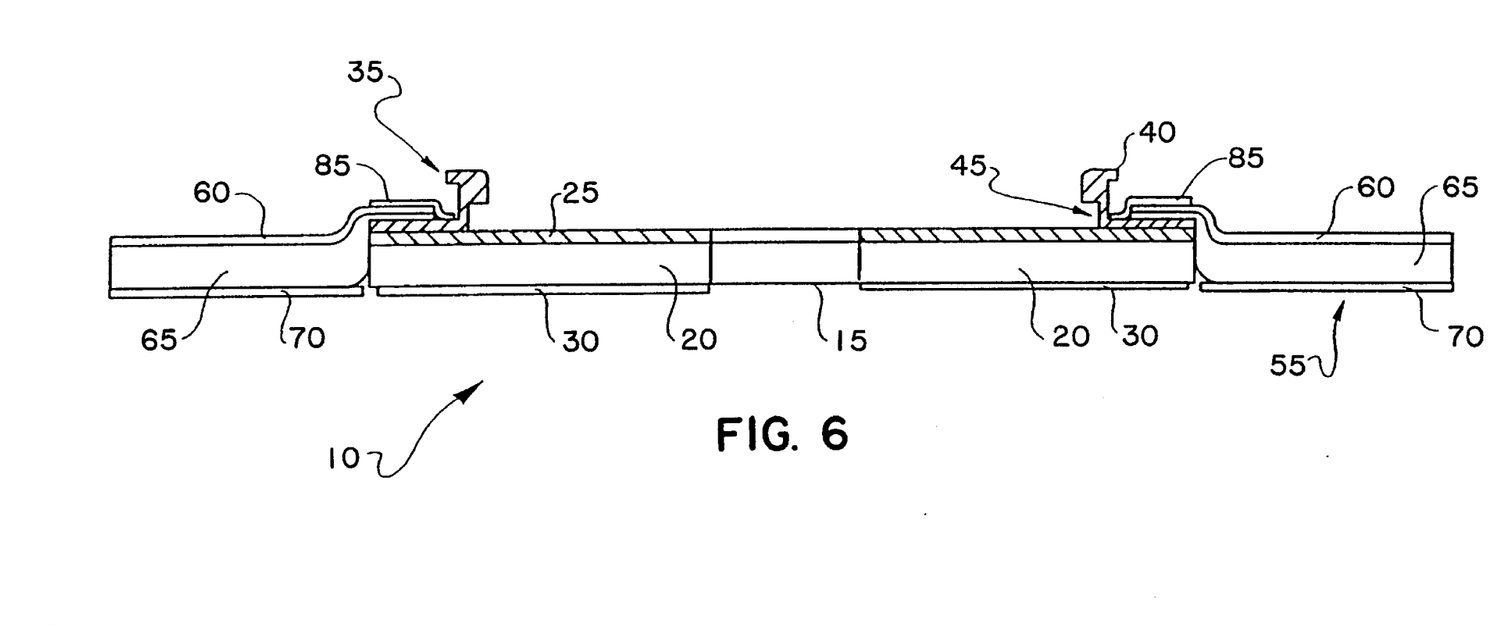
FIG. 6 is an enlarged cross-sectional view of the gasket of FIGS. 4 and 5.

FIGS. 4–6 illustrate an ostomy gasket 10 which includes adhesives made of the polymers of the present invention. This device has a central aperture for placement over the incision and through which fluids may drain. Adjacent to and surrounding the aperture 15 is a layer 20 of an adhesive material which has highly absorbent properties to withstand the moist environment and fluids which drain through the aperture. This layer 20 is preferably made of material such as STOMAHESIVE, which is available from ConvaTech, Skillman, N.J. Alternatively, this layer 20 of absorbent material can be of a pressure-sensitive adhesive in accordance with the invention which includes a high ethylene oxide content. Also, other highly absorbent materials, even ones that do not have adhesive properties, can be used for this component, since the primary function of this layer 20 is to be able to withstand and absorb water or body fluids.

This absorbent material 20 is preferably supported on a polyethylene film 25. When an adhesive material such as STOMAHESIVE or the like is used, the opposite side (or working face) of this layer 20 includes release liner 30 which allows handling of the article without concern as to the absorbent material adhering to unintended surfaces.

The polyethylene film support 25 is secured to a flange 35 which is adapted to receive an ostomy bottle or other container for storing the fluid which passes through aperture 15. Thus, flange 35 includes a lip 40 and corresponding recess 45 to facilitate attachment of the bottle or container thereto. Flange 35 is attached to disk shaped extension 50. A supportive adhesive band 55 in accordance with the invention completely surrounds the periphery of the flange 35. This band 55 includes a polyester fiber backing layer 60 upon which is placed an adhesive such as that of Example 9 of the present application. This adhesive is shown as 65. To prevent the adhesive from sticking to surfaces prior to the desired time of use, a release layer 70 is provided on the side opposite the backing layer (i.e., the adhesive face). As shown in FIG. 5, the backing layer includes cut notches 75 to facilitate removing a portion of the backing 80 and thus more easily expose the adhesive face for attachment to the desired surfaces.

Adhesive band 55 is attached to the top of flange extension 50 and adhered thereto due to the adhesive properties of layer 65. To obtain a more secure connection between band 55 and flange portion 50, a plastic ring 85 is placed upon the backing member 60 of the band 55 and is ultrasonically welded to extension 50 of flange 35.

When the device is to be used, the release layers 70 and 30 are first removed thus exposing the PSA material 65 of band 55 and the absorbent material 20. The PSA material 65 as noted above is skin friendly and provides a secure bond to the skin without damaging it. Thus, the gasket is retained in the desired place despite whether absorbent layer 20 has adhesive characteristics or not. When absorbent layer 20 is made of a highly water absorbent material, it most often does not develop sufficient tack or green strength so that it can be properly secured in place on the patient. Thus, the PSA adhesive 65 provides a secure bonding of the gasket to the patient and holds the absorbent layer in place so that any further bonding due to the adhesive properties of absorbent 20 can occur over time. Again, as noted above, PSA layer 65 allows the skin to breathe so that excessive fluid does not accumulate thereon and cause damage or other detrimental affects to the skin.

The following examples, which are intended to illustrate the invention described herein without unduly restricting it, provide further illustrations of how to select the appropriate components and amounts thereof to form the desired pressure-sensitive adhesives.

EXAMPLES

In order to understand the formulations and properties of the adhesives which are described in these examples, the following abbreviations and test protocols are used.

ABBREVIATIONS:

| | |
|---|---|
| DESMODUR H: | Hexamethylene diisocyanate (Miles, Inc., Perkasie, PA). |
| DESMODUR N 3300: | A polymeric aliphatic isocyanate based on hexamethylene diisocyanate with an NCO content of 21.6% (Miles) |
| DESMODUR W: | An aliphatic diisocyanate; i.e., dicyclohexylmethane-4,4'-diisocyanate (Miles) |
| DEG: | Diethylene glycol (a chain extender). |
| ISON 2181: | Polymeric MDI Functionality 2 (Dow Chemical Company, Midland, MI). |
| MEDIFILM MF428: | An elastic polyurethane film (Bertek: St. Albans, CT). |
| METACURE T12: | Dibutyl tin dilaurate (Air Products: Allentown, PA). |
| PAPI 94: | A diphenylmethane diisocyanate (MDI) containing methylene bisphenyl isocyanate and polymethylene polyphenyl isocyanate (Dow Chemical Company) |
| PAPI 2580: | A polymethylene polyphenylisocyanate that contains methylene diisocyanate (MDI) having an NCO content of 30.8% (Dow Chemical Company). |
| POLY G-26-37: | A polyether diol of a hydroxyl terminated poly (oxyalkylene) polyol (Olin Corporation, Stamford, CT) |
| POLY G-55-28: | An ethylene oxide capped diol having a nominal molecular weight of 4,000 with 85% ethylene oxide end groups (Olin Corporation). |
| POLY PG 55-37: | A difunctional random copolyol containing 35% ethylene oxide and 75% propylene oxide, with 85% ethylene oxide end groups (Olin Corporation). |
| POLY G-55-56: | An ethylene oxide capped diol having a nominal molecular weight of 2,000 with 87% ethylene oxide end groups (Olin Corporation). |
| POLY G-83-34: | A glycerol-based triol having a nominal molecular weight of 4,500 which is a hereto polyether polyol with a high ethylene oxide content (Olin Corporation). |
| XUS15176: | Copolymer of 30% ethylene oxide and 70% propylene oxide, molecular weight 3000 and a functionality of 2 (Dow Chemical Company). |

BALL TACK TEST

Samples are tested according to the Rolling Ball Tack Test method of PSTC-6 in "Test Methods for Pressure-Sensitive Tapes" published by the Pressure-Sensitive Tape Council. A Standard Incline Ramp as specified by PSTC-6 with stainless steel balls was used. The ramp is placed over the pressure-sensitive adhesive sample and the distance from the end of the ramp to the middle point of the sample is measured after releasing the ball down the ramp.

WATER UPTAKE (WU) TEST

The protocol for this test is set forth as follows:

1. Cut ½" disk of material (sample).
2. Weight aluminum weighing dish (W1).
3. Weigh samples (W2).
4. Remove backing from sample and weigh (W3).
5. Place sample with adhesive side up into dish and fill dish with water to submerge sample.
6. Soak sample for 24 hours.
7. Remove sample from dish, shake off excess water and weigh sample.

$$\% \text{ Water Uptake} = \frac{W4 - (W2 - W3) \times 100}{W2 - W3}$$

PEEL TEST

Samples are tested according to the Stainless Steel Plate Peel 180° Test of PSTC-1 in the "Test Methods for Pressure-Sensitive Tapes" published by the Pressure-Sensitive Tape Council. A 1" wide by 4" length strip of sample is applied to a stainless steel plate. A rolling pin is passed back and forth over the sample once and the plate is secured in an Instron Material Tester and the strip peeled at 180° at a speed of 200 mm/min. The force is recorded.

Figure 3:
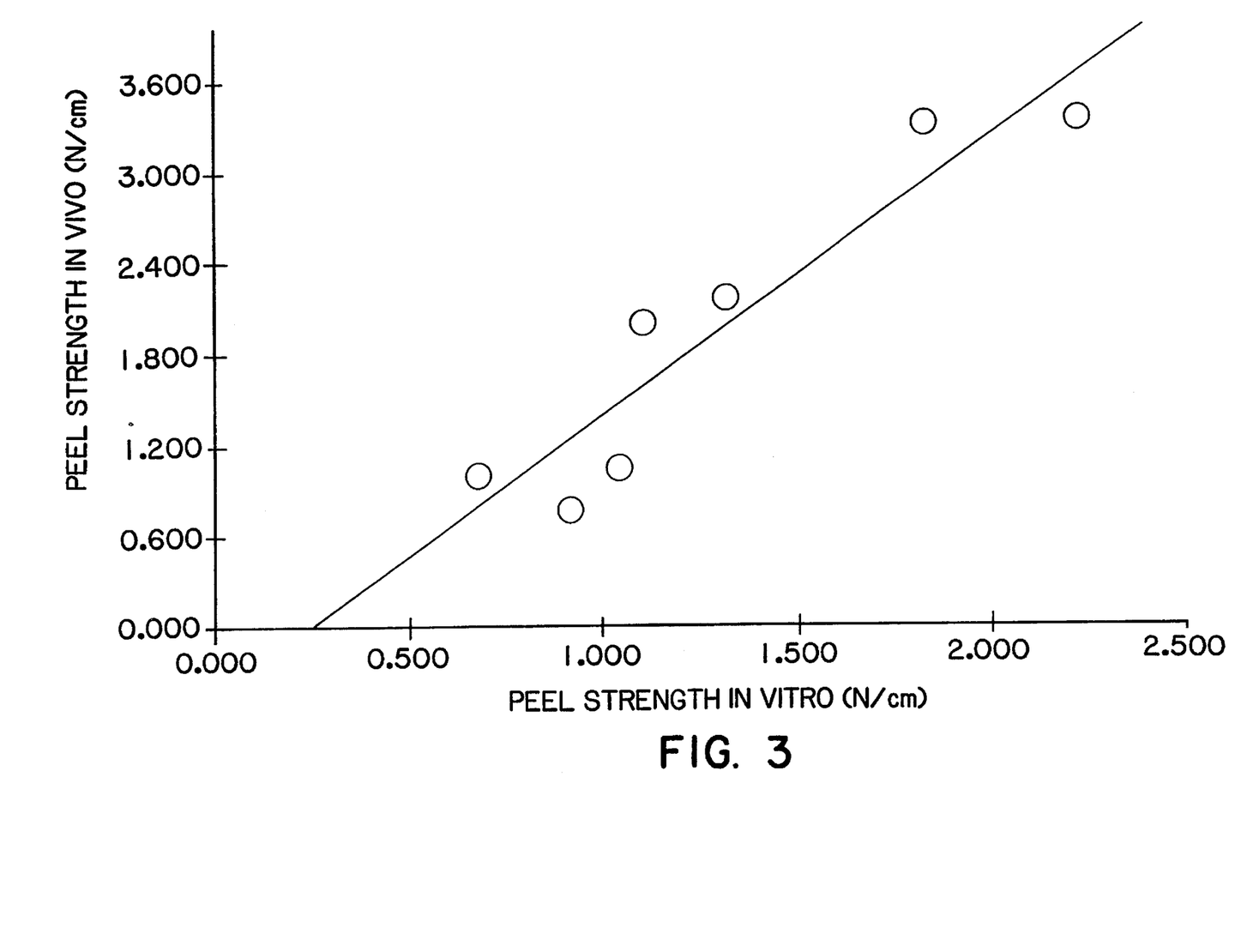
FIG. 3 is a graph showing the correlation between peel strength of pressure-sensitive polyurethane adhesives in vitro versus peel strength in vivo.

As noted above, the peel adhesion of the polyurethane adhesive on human skin is not the same as that on the stainless steel panel, but the former property varies linearly with the latter property, as shown in FIG. 3. Thus, one can conduct peel tests on stainless steel sheets and correlate the results to what is necessary for actual skin adhesion values.

WATER VAPOR TRANSMISSION TEST

ASTM Standard Test Methods of Water Vapor Transmission of Materials Designation: E96-80 was used. The Water Method paragraph 3.2 of the test method was used.

In the Water Method, a dish is prepared containing distilled water and weighings are made to determine the rate of vapor movement through the specimen from the water to a controlled atmosphere.

TEST METHOD FOR PEEL ADHESIONS FROM HUMAN SKIN

Apparatus Used: Instron Material Tester with a load cell capable of accommodating the specified range of force.

Sample: Healthy, clean skin free of creams or lotions.

Sample Preparation: Cut 1"×3" strips of sample from each material to be tested. Remove the Silicone Release Paper (SRP) and apply adhesive side to the inner forearm. The strips are placed in a row down the width of the arm.

Procedure: Samples are removed at appropriate time intervals. The lower ½" end of the sample strip is loosened and affixed to the upper grips with a strip of 1" masking tape. The forearm is placed under the upper grips and the sample strip is removed at a speed of 200 mm/min. The resulting force is recorded and the subject's skin is assessed for any irritation or adhesive residue.

Example 1

Adhesives were made from a polyisocyanate having a functionality of 2.8 and a mixture of di and trifunctional polyols, and the peel adhesion values were measured. The results presented in Table 5 show that the peel adhesion values decrease with an increasing NCO/OH ratio.

TABLE 5

| NCO/OH* RATIO | PEEL STRENGTH N/cm |
|---|---|
| 0.752 | 0.28 |
| 0.702 | 0.94 |
| 0.668 | 1.98 |

*Reactants 1:1 Mixture of Poly G 55-28 and Poly G 83-34 Polyols and PAPI 2580 Polyisocyanate

Example 2

Adhesives were made from a polyisocyanate having a functionality of 2.8 and a mixture of di and trifunctional polyols, and the peel adhesion values were measured. The results presented in Table 6 show that the peel adhesion values decrease as the functionality of the polyol increases. For this example, the addition of a trifunctional polyol (POLY G-83-34) increases the polyol functionality and decreases the peel adhesion.

TABLE 6

| Poly G 55-56[a] % | Poly G 83-34[b] % | NCO/OH Ratio[c] | PEEL STRENGTH N/cm |
|---|---|---|---|
| 90.25 | — | 0.755 | 2.50 |
| 50.63 | 41.15 | 0.756 | 0.56 |
| 90.51 | — | 0.733 | 1.74 |
| 50.96 | 41.04 | 0.732 | 0.77 |

[a]Poly G 55-56 Polyether, functionality 2, 45% ETO content, MW 2000
[b]Poly G 83-34 Polyether, functionality 3, 70% ETO content, MW 4700
[c]Polyisocyanate PAPI 2580, functionality 2.8

Example 3

As noted above, the hydrophilicity of the polyurethane adhesive depends upon the hydrophilicity of the polyol. Thus, polyurethane adhesives prepared from polyols having high ethylene oxide content have a much higher water uptake capacity as shown in Table 7.

TABLE 7

EFFECT OF ETHYLENE OXIDE CONTENT OF THE POLYOL

| Diisocyanate | Polyols | Polyol eto Content % | NCO/OH Ratio | Water Uptake % |
|---|---|---|---|---|
| Isonate 2181 | Poly G 83-34 | 70 | 0.756 | 571 |
| PAPI 94 | Poly G 55-56 | 45 | 0.755 | 282 |
| PAPI 94 | XUS 15176 | 30 | 0.756 | 101 |

Example 4

A mixture of aliphatic isocyanates comprising 1.954 parts of DESMODUR N 3300 (functionality 3.4–3.6) and 1.930 parts of DESMODUR H (functionality 2) were added to a mixture of 40 parts of Poly-G 55-37 and 0.0428 parts of dibutyltin dilaurate (METACURE T-12) and then mixed with a stirrer blade which avoids air bubble trapping. This mixture represented an NCO/OH ratio of 0.8. The mixing was continued at room temperature until a uniform mixture was obtained (about 2–3 min). The mixture started to build heat and viscosity after about 5–10 min after mixing. During this period of time, the mixture was cast on MEDFILM 428 (thermoplastic polyurethane film) to a thickness of 40 mils, and immediately cured into an oven at 102° C. for 5 minutes. The resulting adhesive was completely cured and showed a peel strength of 2.25 newtons/cm. on stainless steel, and had a water uptake of over 200%.

Examples 5–8

The formulations described in Table 8 below were mixed, coated onto the thermoplastic polyurethane film, Medfilm 428), and cured according to the procedure of Example 4. The adhesion and water uptake properties of the resultant adhesive laminates are described in Table 8 below.

TABLE 8

ALIPHATIC POLYURETHANE ADHESIVES

| | Formulation, Parts by Weight | | | | | | | | |
|---|---|---|---|---|---|---|---|---|---|
| Example No. | DESMODUR N 3300 | DESMODUR W | DESMODUR H | POLY G-55-56 | POLY G-55-37 | POLY G-83-34 | METACURE T-12 | Peel Adhesion N/cm | Water Uptake % |
| 6 | 3.914 | — | 1.695 | 50 | — | — | 0.05 | 1.12 | 553 |
| 7 | 3.816 | — | 2.754 | 65 | — | — | 0.065 | 2.25 | 868 |
| 8 | 1.997 | 1.348 | — | — | 40 | — | 0.04 | 0.75 | 246 |
| 9 | — | 0.666 | — | — | — | 20 | 0.02 | 0.45 | 1000 |

Example 9

Polyurethane adhesive prepared for tape application. A NCO-terminated prepolymer mixture was prepared as follows:

A dry three-neck bottom flask was charged with 77.2 parts of POLY G-26-37 polyol, 3.2 parts of DESMODUR N-3300, 12.9 parts of DESMODUR W and 0.38 part of dibutyl tin dilaurate catalyst. The reaction mixture was then heated at 90° C. for about two hours with stirring and under a blanket of dry nitrogen gas. After the reaction was completed, the reaction mixture was allowed to cool to room temperature. To this viscous prepolymer, another 6.3 parts of DESMODUR N-3300 was added with stirring to obtain a homogeneous NCO-terminated prepolymer mixture for preparation of polyurethane adhesives.

The polyurethane adhesive/non-woven fabric tape was prepared by first vigorously mixing 39.3 parts of the NCO-terminated prepolymer mixture and 60.7 of POLY G-26-37 at room temperature for less than one minute. The reaction mass was then cast onto a support release paper to a thickness of about 6 mils. The cast material was then cured in an air circulating oven at 120° C. for three minutes. After cooling to room temperature, a clear pressure-sensitive adhesive slab was obtained, which was then laminated to a thin non-woven fabric.

The lamination was performed by means of a standard rubber/metal nip-roll. The non-woven backed polyurethane adhesive tape had a peel adhesion of 1.2 Newtons/cm and a moisture vapor transmission rate of 1020 g/meter$^2$/24 hours at 37° C. with a 90% relative humidity gradient.

Thus it is apparent from the foregoing description that the objects of this invention have been attained. A novel pressure-sensitive polyurethane adhesive has been invented which contains the desired properties.

We claim:

1. A pressure-sensitive adhesive comprising a polyurethane polymer formed by the reaction of an isocyanate component and a polyol component having a molecular weight between about 1,000 and 10,000, said components being reacted at a molar ratio of isocyanate moieties to hydroxyl moieties of less than one, said polymer being free from any added tackifying and plasticizing agents, said polymer having a glass transition temperature of less than about 0° C., a moisture absorption at equilibrium of at least 20% of its weight, and a peel adhesion to human skin of between about 0.3 and 4 newtons/cm width of the polymer, wherein said isocyanate and said polyol components each have a functionality of at least two and wherein at least one of said components has a functionality that is greater than 2, and further wherein said polyurethane polymer is crosslinked to a crosslink density $\alpha$ of between about $10^{-4}$ and $10^{-3}$ wherein $\alpha$ is defined by the equation $$\alpha \approx \frac{\overset{i=}{\underset{n}{\Sigma}} X_i (F_i - 2)}{(1.05 - r) Mw}$$

where i=1 to n where n is the number of the reactant components;

$X_i$=the mole fraction of the $i^{th}$ component;

$F_i$=the functionality of the $i^{th}$ component;

r=the NCO/OH ratio; and

Mw=the molecular weight of the polyol.

2. The pressure-sensitive adhesive of claim 1 wherein the glass transition temperature is less than about −30° C., the moisture absorption at equilibrium is at least about 100% of its weight, and the peel adhesion is between about 0.5 and 3.5 newtons/cm width of the polymer.

3. The pressure-sensitive adhesive of claim 1 wherein the polyurethane polymer has a moisture vapor transmission rate of at least about 300 grams/meter$^2$/24 hours measured at 37° C. and a 90% relative humidity gradient, and a peel adhesion to human skin of between about 0.5 and 3.5 newtons/cm width of the polymer.

4. The pressure-sensitive adhesive of claim 3 wherein the glass transition temperature is less than about −30° C., and the moisture vapor transmission rate is at least about 500 grams/meter$^2$/24.

5. The pressure-sensitive adhesive of claim 1 wherein the isocyanate component is an aliphatic polyisocyanate and the crosslink density is between about $2 \times 10^{-4}$ and $10^{-3}$.

6. The pressure-sensitive adhesive of claim 1 wherein the isocyanate component is an aromatic polyisocyanate and the crosslink density is between about $4 \times 10^{-4}$ and $9 \times 10^{-4}$.

7. The pressure-sensitive adhesive of claim 1 wherein the molar ratio is between about 0.5 and 0.99.

8. The pressure-sensitive adhesive of claim 1 wherein the molar ratio is between about 0.65 and 0.9.

9. The pressure-sensitive adhesive of claim 1 wherein the polyether polyol is a homopolymer or copolymer containing ethylene oxide or propylene oxide groups.

10. The pressure-sensitive adhesive of claim 1 wherein the polyol component comprises a polyether polyol having a molecular weight of between about 1000 and 10,000 and a functionality of greater than 2 and the isocyanate component has a functionality of 2.

11. The pressure-sensitive adhesive of claim 1 wherein the polyol component is a polyether diol or triol containing at least about 30% by weight of ethylene oxide groups.

12. The pressure-sensitive adhesive of claim 1 wherein the polyol component is a hydroxyl terminated prepolymer.

13. The pressure-sensitive adhesive of claim 1 wherein the isocyanate component is an aliphatic or aromatic diisocyanate or a combination thereof, and the polyol component has a functionality of greater than 2.

14. The pressure-sensitive adhesive of claim 1 wherein the isocyanate component is an isocyanate terminated prepolymer.

15. A method for making a pressure-sensitive adhesive for application to skin which comprises:

providing a mixture of an isocyanate component, having a functionality of at least 2, and a polyol component having a molecular weight of between about 1,000 and 10,000 and also having a functionality of at least 2 at a molar ratio of isocyanate moieties to hydroxyl moieties of less than one;

selecting at least one of the components to have a functionality that is greater than two to facilitate crosslinking; and reacting the isocyanate and polyol components in the presence of a catalyst to form a polyurethane polymer, said polyurethane polymer being free from any added tackifying and plasticizing agents, having a glass transition temperature of less than about 0° C., having a moisture absorption of at least about 20% of its weight and/or a moisture vapor transmission rate of at least about 300 grams/meter$^2$/24 hours measured at 37° C. and 90% relative humidity gradient, and having a peel adhesion to human skin of between about 0.3 and 4 newtons/cm width of the polymer wherein said polyurethane polymer is crosslinked to a crosslink density $\alpha$ of between about $10^{-4}$ and $10^{-3}$ wherein $\alpha$ is defined by the equation:

$$\alpha \approx \frac{\overset{i=1}{\underset{n}{\Sigma}} X_i (F_i - 2)}{(1.05 - r) Mw}$$

where i=1 to n where n is the number of the reactant components;

$X_i$=the mole fraction of the $i^{th}$ component;

$F_i$=the functionality of the $i^{th}$ component;

r=the NCO/OH ratio; and

Mw=the molecular weight of the polyol. transmission rate of at least about 300 grams/meter$^2$/24 hours measured at 37° C. and a 90% relative humidity gradient, and a peel adhesion to human skin of between about 0.3 and 4 newtons/cm width of the polymer.

16. The method of claim 15 which further comprises casting the mixture upon a substrate and heating the mixture at a sufficient temperature and for a sufficient time to form a layer of the polymer.

17. The method of claim 16 wherein the mixture is heated to a temperature of between about 100° and 150° C. for a time of between about 1 to 25 minutes.

18. The method of claim 15 which further comprises providing a polyether polyol containing at least about 30% by weight of ethylene oxide groups in order to form a polymer having a moisture absorption at equilibrium of at least about 20% of its weight.

19. The method of claim 15 which further comprises forming an isocyanate terminated prepolymer by reaction of a portion of the polyol component with the isocyanate component prior to reaction of the prepolymer with the remaining polyol component.

20. The method of claim 15 which further comprises selecting the polyol component to have a hydroxyl functionality of greater than 2 to obtain the desired crosslink density.

21. The method of claim 15 which further comprises selecting the isocyanate component to have an isocyanate functionality of greater than 2 to obtain the desired crosslink density.

22. The method of claim 15 which further comprises providing the polymer in the form of a layer upon a backing material.

23. The method of claim 22 which further comprises providing the polymer in the form of a layer upon a release layer.

* * * * *